US006671935B2

(12) United States Patent
Filion et al.

(10) Patent No.: US 6,671,935 B2
(45) Date of Patent: Jan. 6, 2004

(54) VARYING THE LOOP ENGAGEABILITY OF FASTENER ELEMENT ARRAYS

(75) Inventors: Scott M. Filion, Newmarket, NH (US); Richard J. Schmidt, Roswell, GA (US)

(73) Assignee: Velcro Industries B.V., Netherlands (AN)

( * ) Notice: Subject to any disclaimer, the term of this patent is extended or adjusted under 35 U.S.C. 154(b) by 0 days.

(21) Appl. No.: 10/277,309

(22) Filed: Oct. 22, 2002

(65) Prior Publication Data

US 2003/0041422 A1 Mar. 6, 2003

Related U.S. Application Data

(62) Division of application No. 09/585,942, filed on Jun. 2, 2000.

(51) Int. Cl.[7] .......................... A44B 18/00; B29C 45/04; B32B 3/06
(52) U.S. Cl. .............................. 24/452; 24/442; 24/446; 24/306; 24/304; 264/167; 264/220; 264/221; 428/100
(58) Field of Search .......................... 24/452, 442, 446, 24/450, 306, 304; 264/173.1, 167, 220, 221; 425/165, 164, 471, 134, 70; 428/100

(56) References Cited

U.S. PATENT DOCUMENTS

| 3,312,583 | A |   | 4/1967 | Rochlis ................. 161/62 |
| 3,408,705 | A |   | 11/1968 | Kayser et al. .............. 24/204 |
| 4,672,722 | A | * | 6/1987 | Malamed ................... 24/446 |
| 4,794,028 | A |   | 12/1988 | Fischer |
| 4,872,243 | A |   | 10/1989 | Fischer ...................... 24/442 |
| 5,260,015 | A | * | 11/1993 | Kennedy et al. ............ 264/167 |
| 5,441,687 | A |   | 8/1995 | Murasaki et al. |
| 5,625,930 | A | * | 5/1997 | Takizawa et al. ............ 24/452 |
| 5,664,301 | A | * | 9/1997 | Akeno ...................... 24/452 |
| 5,685,050 | A | * | 11/1997 | Murasaki ................... 24/442 |
| 5,692,271 | A |   | 12/1997 | Provost et al. |
| 5,702,797 | A | * | 12/1997 | Sakakibara et al. ......... 428/100 |
| 5,755,016 | A |   | 5/1998 | Provost |
| 5,875,527 | A |   | 3/1999 | Lacey et al. |
| 5,922,222 | A |   | 7/1999 | Jens et al. |
| 5,933,927 | A |   | 8/1999 | Miller et al. ................ 24/452 |
| 5,948,337 | A | * | 9/1999 | Sakakibara et al. ......... 264/167 |
| 6,061,881 | A | * | 5/2000 | Takizawa et al. ............ 24/446 |
| 6,063,067 | A | * | 5/2000 | Takizawa et al. ............ 24/452 |
| 6,127,018 | A | * | 10/2000 | Akeno et al. ............... 428/100 |
| 6,163,939 | A | * | 12/2000 | Lacey et al. ................ 24/452 |
| 6,258,311 | B1 | * | 7/2001 | Jens et al. .................. 264/220 |
| 6,432,339 | B1 | * | 8/2002 | Jens et al. .................. 264/167 |

FOREIGN PATENT DOCUMENTS

| EP | 0464754 | * | 1/1992 | .................. 24/442 |
| EP | 0766934 A2 |   | 9/1997 | |
| WO | 92/00023 | * | 1/1992 | .................. 24/442 |
| WO | WO 95/01863 |   | 1/1995 | |

\* cited by examiner

Primary Examiner—Victor Sakran
(74) Attorney, Agent, or Firm—Fish & Richardson P.C.

(57) ABSTRACT

An easy-to-grip diaper fastener tab has an array of hook-shaped fastener elements arranged in parallel rows, each fastener element including a stem and a crook extending from the stem in a predetermined direction to a distal tip. The array includes a plurality of rows of fastener elements arranged such that, in each row, all of the crooks face in the same direction and parallel to the direction of the row, with the crooks of adjacent rows facing in opposite directions. The longitudinal spacing between opposing tips of adjacent hooks of adjacent rows is greater in a first portion of the array than the longitudinal spacing between opposing tips of adjacent hooks of adjacent rows in a second portion of the array, such that the crooks of the hooks of the first portion are more exposed for engaging loops than the crooks of the hooks of the second portion. Methods and molds for forming such arrays are also provided.

6 Claims, 4 Drawing Sheets

VARYING THE LOOP ENGAGEABILITY OF FASTENER ELEMENT ARRAYS

This application is a divisional (and claims the benefit of priority under 35 USC 120) of U.S. application Ser. No. 09/585,942, filed Jun. 2, 2000. The disclosure of the prior application is considered part of (and is incorporated by reference in) the disclosure of this application.

BACKGROUND OF THE INVENTION

The invention relates to varying the loop engageability of arrays of molded fastener elements, and to the formation of fastener products with exposed grip flanges.

Hook components for hook and loop fastening include a base from which tiny fastener elements (e.g., hook-shaped or mushroom-shaped elements) extend in an array. Hook components with hook-shaped elements may be formed by integrally molding the base and fastener elements in a continuous process employing a mold roll that includes a set of stacked disk-shaped mold plates having fastener-shaped cavities defined at their peripheries, e.g., as described in U.S. Pat. No. 4,794,028 (Fischer), the full disclosure of which is incorporated herein by reference. Hook components may also be injection molded as discrete parts. In the Fischer process, it is generally preferable that the entire molding region of the mold roll include an even distribution of mold cavities, to promote uniform resin flow and molding pressures over the mold roll surface and also to avoid uneven demolding stresses that could distort the fastener. To produce fastener products of the same resin but with different loop engagement characteristics, manufacturers either vary the hook density by changing the spacing between adjacent rows of hooks, or replace the mold plates with others having a different hook cavity shape or in-row spacing.

To form a closure, male fastener elements engage overlying female fastener elements. When the male element is hook-shaped, the fastener element will individually exhibit directional shear strength, i.e., the shear strength in one direction will be significantly higher than in other directions. In some applications it is desirable that the array of fastener elements exhibit bi-directional shear strength, i.e., shear strength substantially equal in each of two opposite directions. To accomplish this, some fastener products include arrays of hooks in which a plurality of rows of fastener elements are arranged so that, in each row, all of the crooks face in the same direction and parallel to the direction of the row, and so that the crooks of adjacent rows face in opposite directions, as shown in FIG. 1.

It is often desirable for a hook and loop fastener to have areas in which there is no engagement or a reduced strength engagement of the two sides of the fastener. Such areas may, for example, be associated with a gripping tab to enable the user to more easily separate the two parts of the fastener.

SUMMARY OF THE INVENTION

The present invention features, in several aspects, an array of hook-shaped fastener elements in which the relative spacing between adjacent hooks varies across the array such that some of the fastener elements are rendered less capable of engagement with loop elements than other fastener elements.

In preferred fastener products, the hook elements are arranged so that some of the hook elements interfere with adjacent hook elements to prevent engagement of the hook elements with loop elements. Advantageously, for fastener products that are molded on mold rolls that include a stack of registered mold plates, e.g., as described in U.S. Pat. No. 4,794,028 (a "Fischer process"), this arrangement can be accomplished by simply adjusting the registration of the mold plates, without the need for other process or tooling changes.

In one aspect, the invention features an array of hook-shaped fastener elements arranged in parallel rows, each fastener element including a stem and a crook extending from the stem in a predetermined direction to a distal tip. The array includes a plurality of rows of fastener elements arranged such that, in each row, all of the crooks face in the same direction and parallel to the direction of the row, and such that the crooks of adjacent rows face in opposite directions. The longitudinal spacing between opposing tips of adjacent hooks of adjacent rows is greater, in a first portion of the array, than the longitudinal spacing between opposing tips of adjacent hooks of adjacent rows in a second portion of the array. As a result, the crooks of the hooks of the first portion of the array are more exposed for engaging loops than the crooks of the hooks of the second portion of the array.

In preferred implementations, the crooks of the hooks of adjacent rows in the second portion of the array overlap each other in side profile to interfere with the ability of the crooks to engage loop elements.

In another aspect, the invention features a fastener product that includes (a) a first fastener component comprising a common base and an array of hook-shaped fastener elements arranged in parallel rows on the common base, and (b) a second fastener element, comprising a common base and a plurality of loops extending from the base for engagement with the hooks. Each fastener element includes a stem and a crook extending from the stem in a predetermined direction to a distal tip, and the array includes a plurality of rows of fastener elements, arranged so that, in each row, all of the crooks face in the same direction and parallel to the direction of the row, the crooks of adjacent rows face in opposite directions. The longitudinal spacing between opposing tips of adjacent hooks of adjacent rows is greater, in a first portion of the array, than the longitudinal spacing between opposing tips of adjacent hooks of adjacent rows in a second portion of the array. As a result, the crooks of the hooks of the first portion of the array are more exposed for engaging loops than the crooks of the hooks of the second portion of the array.

In preferred implementations, the product includes a strip of fastener tabs or a fastener tape.

In some cases, the product includes a personal care product. By "personal care product" as used within this patent application, we mean diapers, training pants, swim wear, absorbent underpants, adult incontinence products and feminine hygiene products In another aspect, an absorbent article is provided. The article has a flexible sheet for fitting about the body of a wearer, the flexible sheet having a first waist portion and a second waist portion. A first fastener element is coupled to the first waist portion, having a common base and a plurality of loops extending from the base. A second fastener component is coupled to the second waist portion such that the second fastener component can be brought into contact with the first fastener element when the first waist portion and the second waist portion are fitted about the body of a wearer. The second fastener component has a common base and an array of hook-shaped fastener elements arranged in parallel rows on the common base, with the fastener elements arranged as described above so as to enhance the grippability of the second fastener component.

In another aspect, the invention features a method of forming an array of fastener elements extending from a common base. The method includes providing a mold having a mold surface from which an array of fixed mold cavities extend inwardly. Each mold cavity defines a hook including a stem and a crook extending from the stem in a predetermined direction, with the array including a plurality of rows of cavities arranged such that, in each row, all of the crooks face in the same direction and parallel to the direction of the row, and with the crooks of adjacent rows face in opposite directions. The registration of adjacent rows is adjusted so that the longitudinal spacing between opposing tips of adjacent hooks of adjacent rows in a first portion of the array is greater than the longitudinal spacing between opposing tips of adjacent hooks of adjacent rows' in a second portion of the array, such that the crooks of the hooks of the first portion are more exposed for engaging loops than the crooks of the hooks of the second portion. Moldable resin is delivered to the mold, thereby filling the mold cavities and forming the common base. The resin is solidified in the cavities to form the fastener elements, which are then removed from their corresponding fixed mold cavities by pulling the common base away from the mold surface.

In some implementations the method further includes forming the mold cavities by aligning a plurality of mold plates in face to face relation, registered openings in the aligned mold plates defining the mold cavities.

The adjusting step may include rotating at least some of the mold plates relative to other mold plates.

In some cases the mold plates are disk-shaped and, when aligned, form a mold roll, the mold cavities extending inwardly from a peripheral surface of the mold roll.

The delivering step includes, in some embodiments, extruding molten resin into a nip defined between the mold roll and a pressure roll.

In another aspect of the invention, a method is provided for varying the loop engagement characteristics of a molded fastener product produced with a set of mold plates arranged in face-to-face relation to form an array of fastener element mold cavities, with each mold plate defining one of many rows of cavities of the array. The method includes positioning the mold plates to purposefully set the longitudinal registration of adjacent rows of the array to decrease longitudinal spacing between adjacent fastener element cavities of adjacent rows, to produce a fastener product with at least a region of an array of fastener elements having a lower loop engageability than a fastener product molded with the mold plates in a different position.

The invention also features, in another aspect, a mold for forming a fastener device. The mold has a mold body with a surface on which a common base can be molded, and defines an array of mold cavities extending into the mold body from the surface. The mold cavities are arranged in parallel rows, with each fastener element including a stem and a crook extending from the stem in a predetermined direction to a distal tip. The array includes a plurality of rows of fastener elements arranged such that, in each row, all of the crooks face in the same direction and parallel to the direction of the row, with the crooks of adjacent rows facing in opposite directions. The longitudinal spacing between opposing tips of adjacent hooks of adjacent rows in a first portion of the array is greater than the longitudinal spacing between opposing tips of adjacent hooks of adjacent rows in a second portion of the array, such that the crooks of the hooks of the first portion are more exposed for engaging loops than the crooks of the hooks of the second portion.

The invention also features a strip of continuously molded fastener tape and a die cut strip of fastener tabs, having the features described above.

In yet another aspect, the invention features an array of hook-shaped fastener elements arranged in parallel rows, each fastener element including a stem and a crook extending from the stem in a predetermined direction to a distal tip, the array having a substantially constant hook density over its surface, and a first portion of the array being constructed to engage loops to a greater extent than a second portion of the array.

In a further aspect, the invention features an array of male fastener elements arranged in parallel rows, each fastener element including a stem and a loop-engaging portion extending from the stem, the array including a plurality of rows of fastener elements. The longitudinal spacing between loop-engaging portions of opposing pairs of fastener elements of adjacent rows in a first portion of the array is greater than the longitudinal spacing between loop-engaging portions of opposing pairs of fastener elements of adjacent rows in a second portion of the array, such that the loop-engaging portions of the fastener elements of the first portion are more exposed for engaging loops than the loop-engaging portions of the fastener elements of the second portion.

In some implementations the male fastener elements are mushroom shaped.

The invention also features an array of male fastener elements arranged in parallel rows, each fastener element including a stem and a loop-engaging portion extending from the stem, the array having a substantially constant hook density over its surface, and a first portion of the array being constructed to engage loops to a greater extent than a second portion of the array.

The invention can provide, inter alia, the advantage of increasing the grippability of engaged fastener tabs without increasing their manufacturing costs. This can be particularly valuable on diapers and other garments, and on fasteners securing emergency medical or fire-fighting equipment. In another sense, the invention can provide the advantage of providing a grip tab with a reduced, but not negligible, amount of loop engageability, such that the grip tab can itself be lightly secured to a loop surface. As applied to diaper tabs, this can make the tab less susceptible to being manipulated by an infant or becoming undesirably released during infant movement. In conjunction with the multiple-plate molding method, where each plate forms one of several rows of fastener elements, the invention is readily implemented by shifting the longitudinal registration of adjacent plates to skew the spacing of adjacent fastener elements to either enhance or degrade their loop engageability. Such registration manipulation is also useful for enabling the molding of fastener products with differing loop engagement characteristics with a single set of mold plates. Such plates can be very expensive to manufacture, and a shift in registration can be much less expensive than having multiple sets of plates of different hook cavity shapes or in-row spacings.

Other features and advantages of the invention will be apparent from the following description of a presently preferred embodiment, and from the claims.

BRIEF DESCRIPTION Of THE DRAWINGS

FIG. 3 is a cross-sectional view taken along line 3—3 in FIG. 2. FIG. 3A further illustrates engagement of hook elements with loops.

FIG. 4 is a cross-sectional view taken along line 4—4 in FIG. 2. FIG. 4A further illustrates attempted engagement of hook elements with loops.

DESCRIPTION Of EMBODIMENTS

Figure 2:
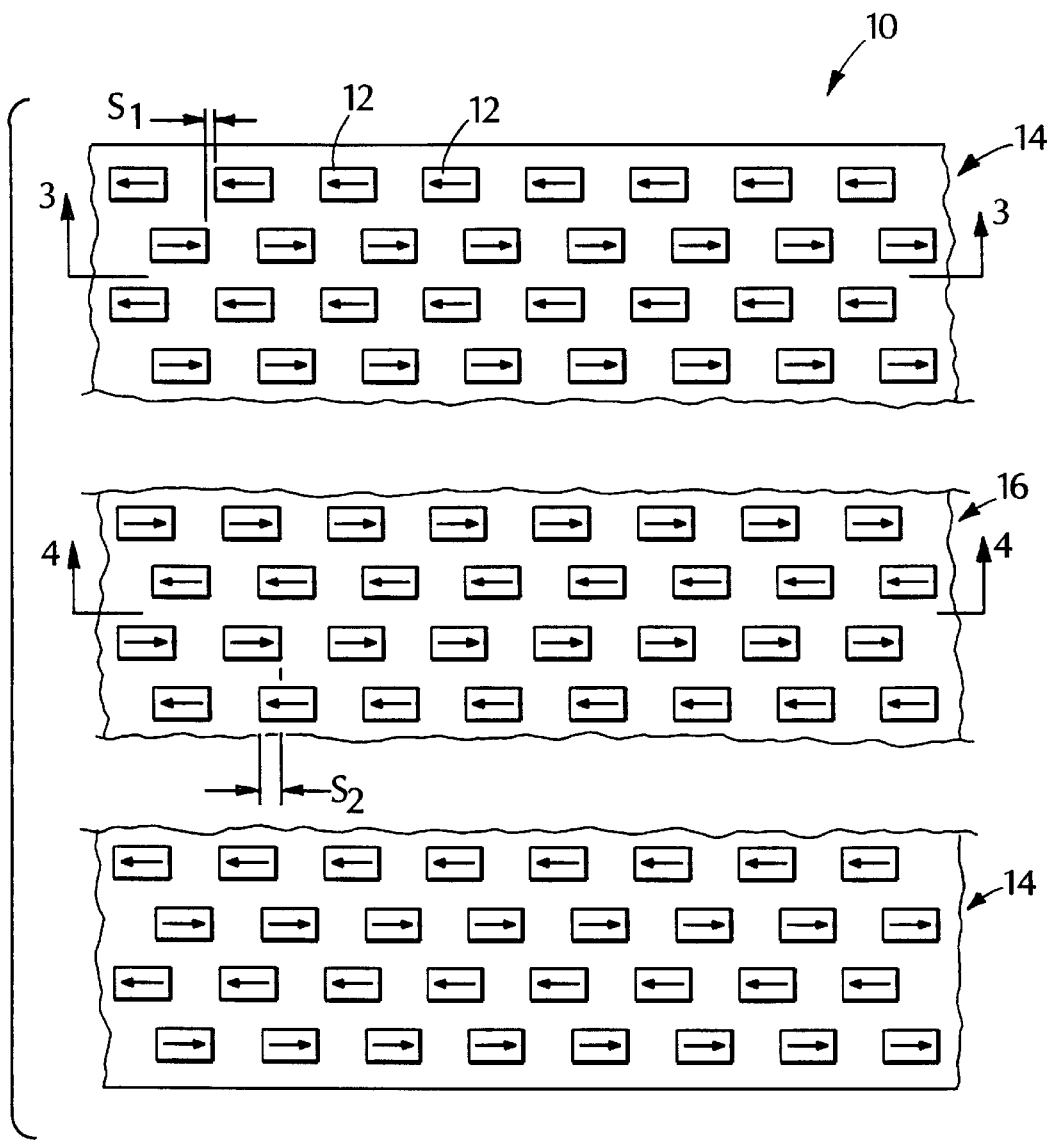
FIG. 2 is a top view of an array of hook elements having regions of high and low engageability with loop elements.

Referring to FIG. 2, a continuous array 10 of hook-shaped fastener elements 12 (shown in outline, with arrows pointing toward hook tips) extend from an integrally molded, sheet-form base 11. Across its width, fastener array 10 includes fastening regions 14, in which the fastener elements 12 are arranged to have a relatively high engageability with mating elements such as loops, and a gripping region 16, in which the fastener elements 12 are arranged to have a relatively low engageability for mating elements.

Figure 3A:
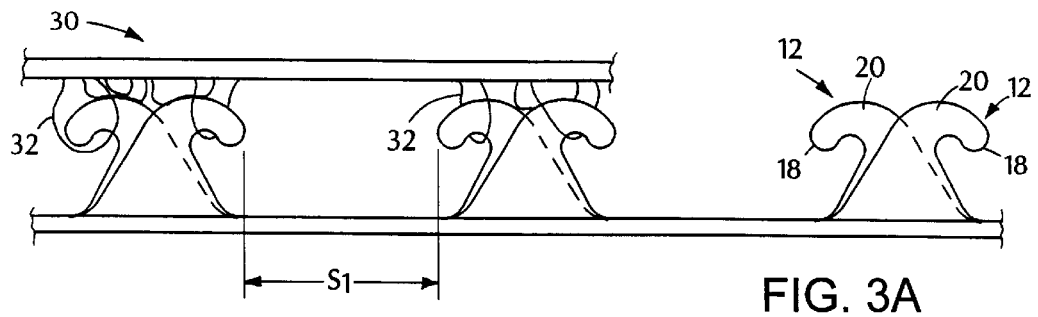
FIGS. 3 and 3A are cross-sectional side views of adjacent rows of hook elements arranged for engagement with loop elements.
Figure 3:
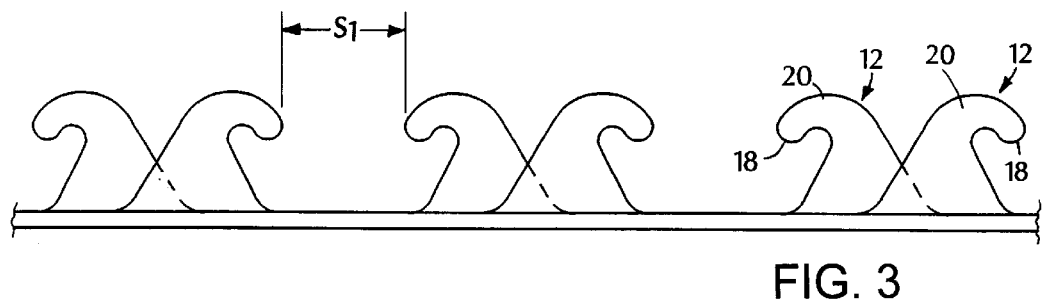

Regions 14 and 16 have parallel longitudinal rows of hooks 12 with the hooks of each row oriented in a uniform direction (as indicated by the arrows in FIG. 2). The relative engageability with mating elements (e.g., loops) of regions 14, 16 is determined by the relative spacing between hooks of adjacent rows. In regions 14, the hooks of adjacent rows are longitudinally spaced to enable a mating loop to readily extend between the hooks and be snared by the re-entrant hook tips, as is well known in the prior art and illustrated in FIG. 3A, for example. The opposing crooks of adjacent hooks of adjacent rows are spaced apart longitudinally to form a gap of width "$S_1$" for receiving loops 32 that extend, for example, from a mating loop component 30 across the adjacent rows of hooks for engagement by the hook crooks (FIG. 3A). FIG. 3 shows another arrangement of hooks arranged to form longitudinal gaps of width "$S_1$" for receiving loops.

Figure 4:
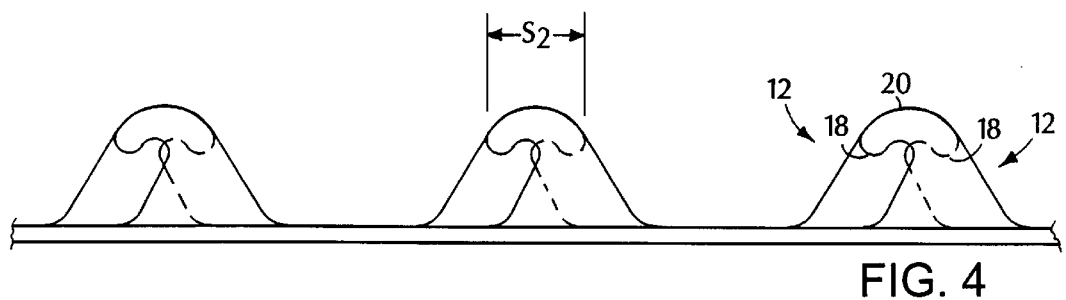
FIGS. 4 and 4A are cross-sectional side views of two adjacent rows of hook elements in first and second arrays, respectively, of hook elements arranged for diminished loop engageability.
Figure 4A:
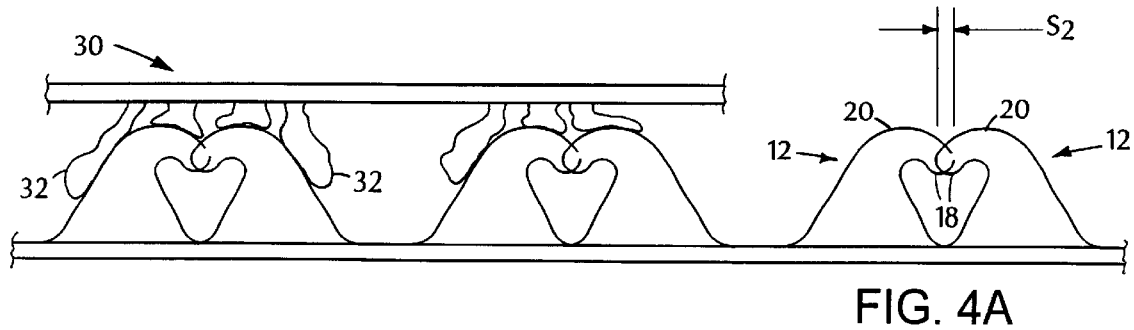

In comparison and referring back to FIG. 2, in gripping region 16 hooks 12 of adjacent rows are longitudinally spaced such that adjacent, opposing crooks longitudinally overlap a distance "$S_2$" (see also FIGS. 4 and 4A) to restrict clearance between the engageable crooks 20 of the hooks 12. As shown in FIG. 4A, individual loops 32 are generally prevented from passing between the adjacent hook tips 18 and are thus less likely to engage hooks 12 than in the fastening regions of the hook array. With fewer engagements of loops with hooks, gripper region 16 is relatively easier to separate from mat 30 than are fastener regions 14 (FIG. 2).

As noted above, if the fastener array is formed using a Fischer process, the regions of relatively low engageability 16 can be formed by rotationally indexing the mold plates that form alternating rows of cavities to cause the longitudinal spacing between tips of the hook cavities to be relatively closer than the longitudinal spacing of the tips in the high loop engageability (i.e., normal registration) areas of the mold.

Figure 1:
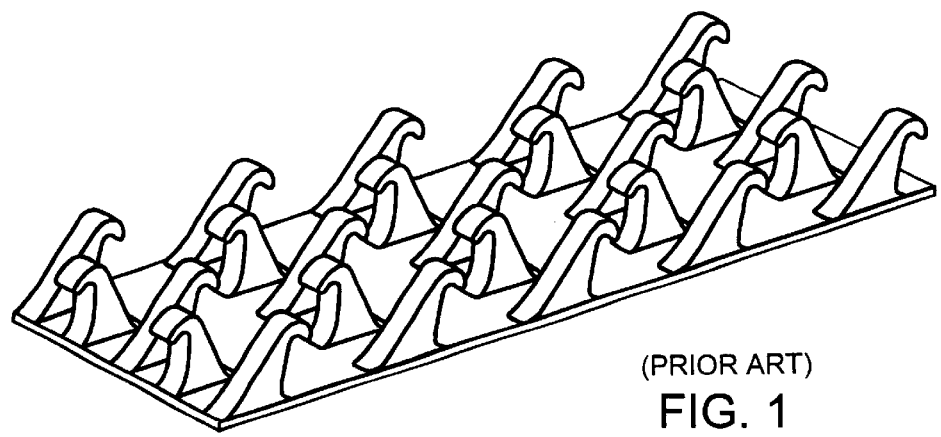
FIG. 1 is a perspective view of an array of hook elements arranged in a conventional manner.
Figure 5:
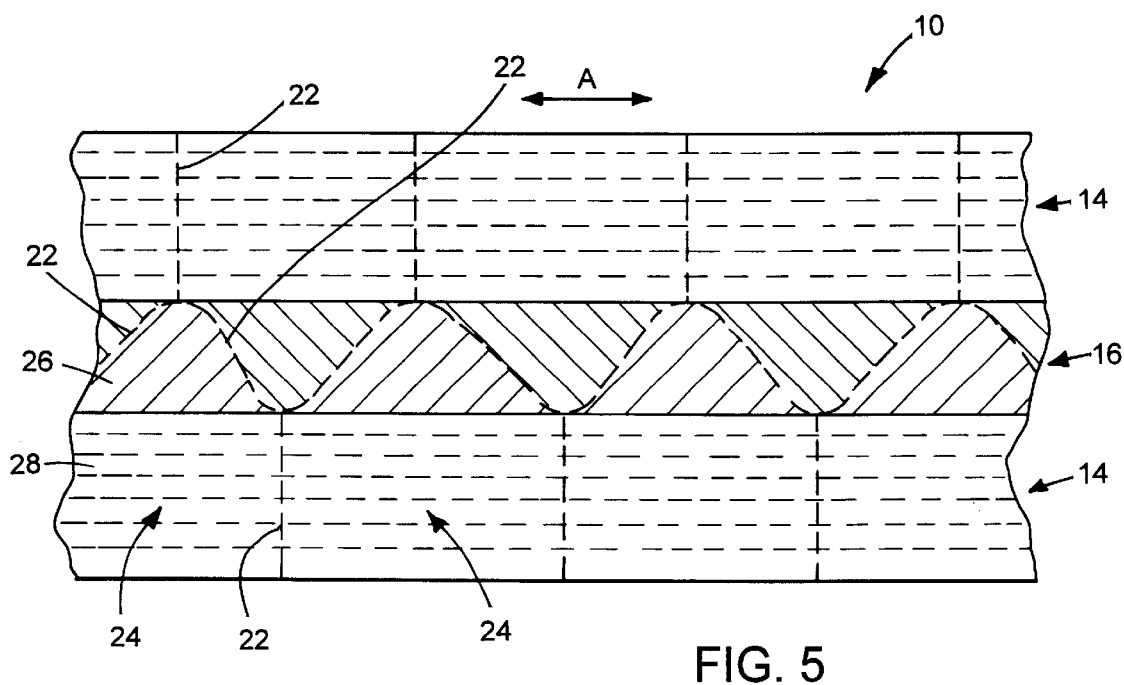
FIG. 5 is a schematic top view of the array of FIG. 2 after die cutting to form a strip of fastener tabs.

As shown in FIG. 5, the array shown in FIG. 2 and described above can be die cut along dashed lines 22 to form a strip of fastener tabs 24, each fastener tab having a grip portion 26 (shown cross-hatched) that has a relatively low loop engageability and allows the fastener tab to be easily disengaged by pulling the grip portion, and a fastening portion 28 that has a relatively high loop engageability for securing the fastener tab to a loop material. The "longitudinal direction" of the product is shown by arrow "A".

Figure 6:
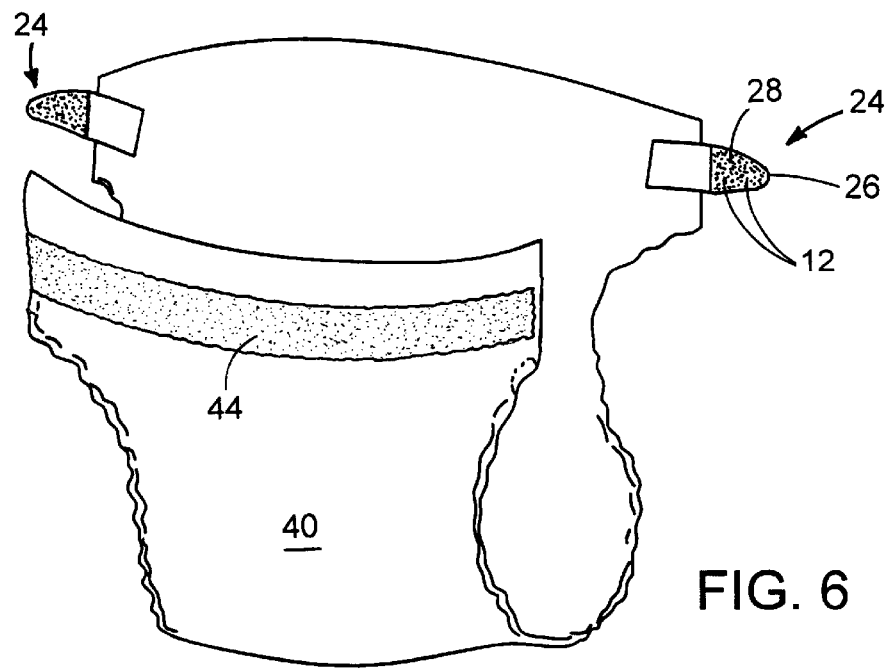
FIG. 6 is a perspective view of a diaper equipped with diaper tabs having fastener tabs of the present invention.
Figure 7:
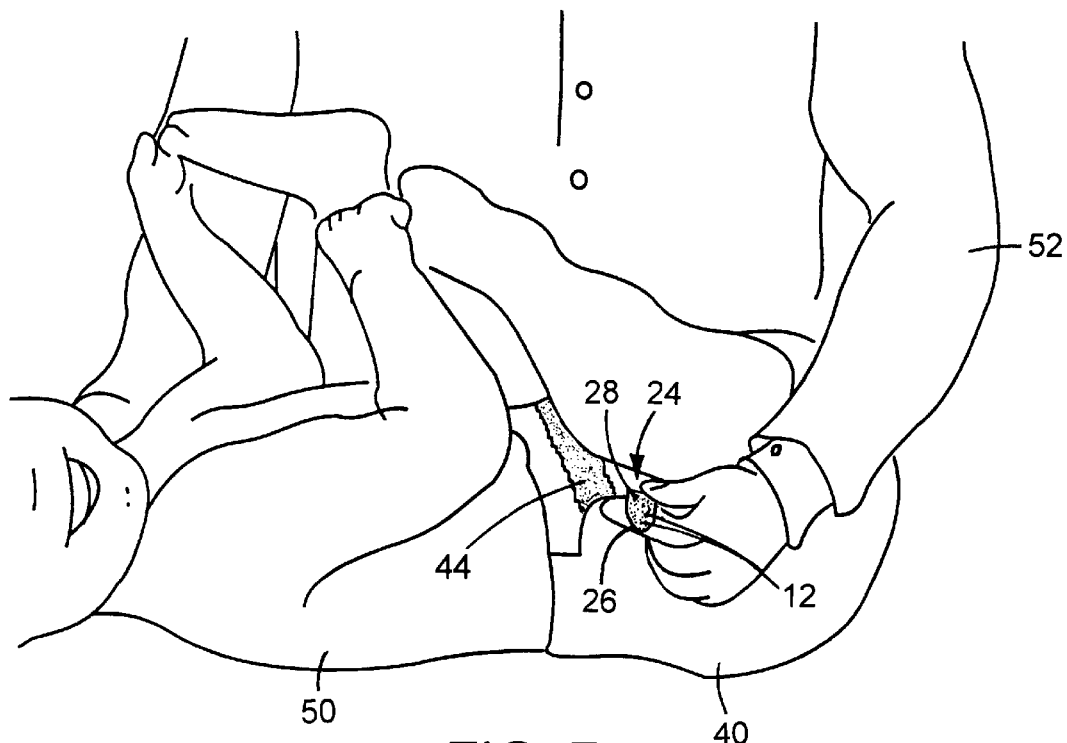
FIG. 7 is a perspective view of the diaper of FIG. 6 being removed from an infant.

The easily disengaged grip portion 26 is advantageous for many applications. For example, as shown in FIG. 6, fastener tabs 24 may be attached to a diaper 40 for fastening the diaper about a wearer. Diaper 40 is equipped with a fastener element engaging region having loops 44 for engaging the fastener elements 12 of the fastener tab 24. As illustrated in FIG. 7, with the diaper 40 secured about a wearer 50 by engagement of the fastener elements 12 of fastener tab 24 to loops 44, the user 52 can readily grasp the grip portion 26 of the fastener tab 24 due to its low loop engageability. Subsequently, user 52 can peel the grip portion away from loops 44 to disengage the fastening region 28 of fastener tab 24 from loops 44. With the fastener tab fully released the diaper can be removed from the wearer or re-secured about the wearer by re-engaging the fastener elements 12 of fastener tab 24 with the loops 44.

Other embodiments are within the claims. For example, the fastener elements may have multiple, laterally directed tips. The fastener element array of varying engageability may be attached to a loop material to form a self-engageable fastener product. The fastener elements may be purposefully arranged such that the engageability variation occurs in the direction along which the hook tips extend, although such an arrangement does not share the advantage of being readily molded in rows with Fischer-type hook plates of constant hook cavity spacing.

What is claimed is:

1. A method of forming an array of fastener elements extending from a common base, the method comprising, providing a mold having a mold surface from which an array of fixed hook mold cavities extend inwardly, each mold cavity defining a stem and a crook extending from the stem to a tip in a predetermined direction, the array including a plurality of longitudinal rows of cavities arranged such that, in each row, all of the crooks face in the same direction and parallel to the direction of the row, with the crooks of adjacent rows facing in opposite directions;

adjusting the registration of adjacent rows so that the longitudinal spacing between opposing tips of adjacent mold cavities of adjacent rows in a first portion of the array being greater than the longitudinal spacing between opposing tips of adjacent mold cavities of adjacent rows in a second portion of the array, for molding an array of hooks having regions of relatively high and low loop engageability;

delivering moldable resin to the mold, thereby filling the mold cavities and forming the common base;

solidifying the resin in the cavities to form the fastener elements; and removing the solidified fastener elements from their corresponding fixed mold cavities by pulling the common base away from the mold surface.

2. The method of claim 1 further including forming the mold cavities by aligning a plurality of mold plates in face to face relation, registered openings in the aligned mold plates defining the mold cavities.

3. The method of claim 2 wherein said adjusting step includes rotating at least some of said mold plates relative to other mold plates.

4. The method of claim 2 wherein said mold plates are disk-shaped and, when aligned, form a mold roll, said mold cavities extending inwardly from a peripheral surface of said mold roll.

5. The method of claim 4 wherein said delivering step comprises extruding molten resin into a nip defined between said mold roll and a pressure roll.

6. A method of varying the loop engagement characteristics of a molded fastener product produced with a set of mold plates arranged in face-to-face relation to form an array of fastener element mold cavities, with each mold plate defining one of many rows of cavities of the array, the method including positioning the mold plates to purposefully set the longitudinal registration of adjacent rows of the array to decrease longitudinal spacing between adjacent fastener element cavities of adjacent rows, to produce a fastener product with at least a region of an array of fastener elements having a lower loop engageability than a fastener product molded with the mold plates in a different position.

* * * * *